United States Patent [19]
Rohe et al.

[11] 3,954,829
[45] May 4, 1976

[54] HALOGENATED 4-TRIFLUOROMETHYL-4'-CYANO-DIPHENYL-ETHER COMPOUNDS

[75] Inventors: Lothar Rohe, Wuppertal; Jürgen Schramm, Dormagen; Erich Klauke, Odenthal-Hahnenberg; Ludwig Eue; Robert Rudolf Schmidt, both of Cologne, all of Germany

[73] Assignee: Bayer Aktiengesellschaft, Leverkusen, Germany

[22] Filed: June 26, 1974

[21] Appl. No.: 483,333

[30] Foreign Application Priority Data
July 3, 1973   Germany.............................. 2333848

[52] U.S. Cl. .................... 260/465 F; 71/98; 71/105
[51] Int. Cl.² ........................................ C07C 121/75
[58] Field of Search ............................. 260/465 F

[56] References Cited
UNITED STATES PATENTS
3,702,862   11/1972   Mine et al. .................... 260/465 F
3,798,276   3/1974   Bayer et al. .................... 260/465 X Primary Examiner—Lewis Gotts
Assistant Examiner—Dolph H. Torrence
Attorney, Agent, or Firm—Burgess, Dinklage & Sprung

[57] ABSTRACT

Halogenated 4-trifluoromethyl-4'-cyano-diphenyl-ether compounds of the formula

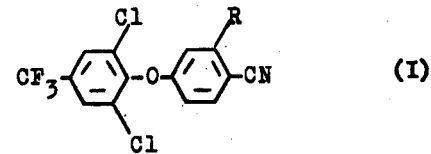

(I)

in which
R is hydrogen, halogen, alkyl of from 1 to 4 carbon atoms, alkoxy of from 1 to 4 carbon atoms or alkylthio of from 1 to 4 carbon atoms, are outstandingly effective as herbicides, particularly as selective herbicides.

7 Claims, No Drawings

HALOGENATED 4-TRIFLUOROMETHYL-4'-CYANO-DIPHENYL-ETHER COMPOUNDS

The present invention relates to certain new halogenated 4-trifluoromethyl-4'-cyano-diphenyl-ether compounds, to herbicidal compositions containing them, and to herbicidal applications using them.

It is known that 2,4-dichloro-4'-cyano-diphenyl-ether and 2,4,6-trichloro-4'-cyano-diphenyl-ether can be used for combating weeds; see German Offenlegungsschrift (German Published Specification) 1,912,000; 2,4-dichloro-4'-nitro-diphenyl-ether disclosed in U.S. Pat. No. 3,080,225 and sold under the name Nitrofen is also known. However, these compounds are not active against all weeds, especially if low amounts and low concentrations are used; for example, they have a low activity against species of Echinochloa, such as *Echinochloa crus galli*, which occurs as a weed in rice, and against species of Eleocharis, such as *Eleocharis palustris*.

The present invention provides halogenated 4-trifluoro-methyl-4'-cyano-diphenyl-ethers of the formula

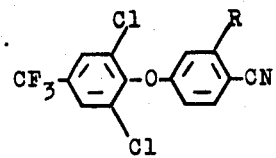

(I)

in which
R is hydrogen, halogen, alkyl of from 1 to 4 carbon atoms, alkoxy of from 1 to 4 carbon atoms or alkylthio of from 1 to 4 carbon atoms.

If R is alkyl, alkoxy or alkylthio, it preferably contains up to 3 carbon atoms; preferred examples of R in this case are methyl, ethyl, methoxy, ethoxy, methylmercapto and ethylmercapto.

Surprisingly, the halogenated 4-trifluoromethyl-4'-cyano-diphenyl-ethers according to the invention display a substantially greater herbicidal action than the compounds known in the art, such as 2,4-dichloro-4'-cyanodiphenyl-ether, 2,4,6-trichloro-4'-cyano-diphenyl-ether and 2,4-dichloro-4'-nitro-diphenyl-ether. The compounds according to the invention thus represent an enrichment of the art.

The invention also provides a process for the production of a halogenated 4-trifluoromethyl-4'-cyano-diphenyl-ether of formula (I) in which a. a 4-halobenzotrifluoride of the formula

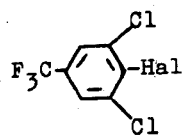

(II)

in which
Hal represents halogen
is reacted with a phenolate of the formula

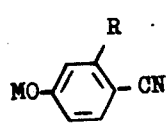

(III)

in which
R has the above-mentioned meaning; and
M represents an alkali metal,
optionally in the presence of an aprotic solvent; or (if R in formula (I) does not represent alkylthio)

b. a diphenyl-ether of the formula

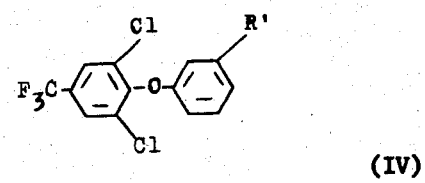

(IV)

in which
R' has the meaning given above for R in formula (I) with the exception of alkylthio,
is reacted with halogen (preferably bromine), optionally in the presence of a diluent, and the 4'-halo-diphenyl-ether obtained thereby of the formula

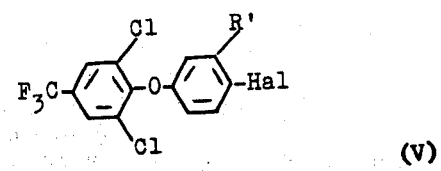

(V)

in which
R' has the above-mentioned meaning; and Hal represents halogen, preferably bromine, is reacted with cuprous (i.e. copper-I) cyanide, optionally in the presence of a diluent; or c. a diphenyl ether of the formula

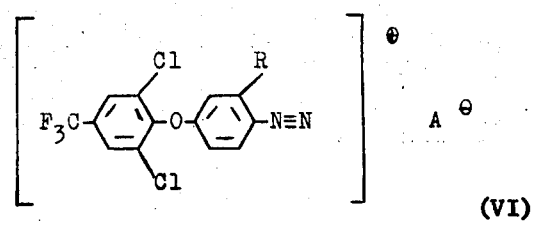

(VI)

in which
R has the above-mentioned meaning; and A represents a mineral acid anion, is reacted with alkali metal cyanide and/or cuprous cyanide, optionally in the presence of a diluent.

If, in accordance with process variant (a), 3,4,5-trichlorobenzotrifluoride and sodium p-cyanophenolate are used as starting compounds, the course of the reaction can be represented by the following formula scheme:

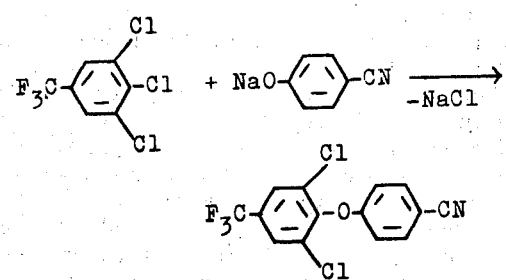

If, according to (the two-stage) process variant (b), 2,6-dichloro-4-trifluoromethyl-3'-methyl-diphenyl-ether and bromine, as well as cuprous cyanide, are used as starting compounds, the course of the reaction can be represented by the following formula scheme:

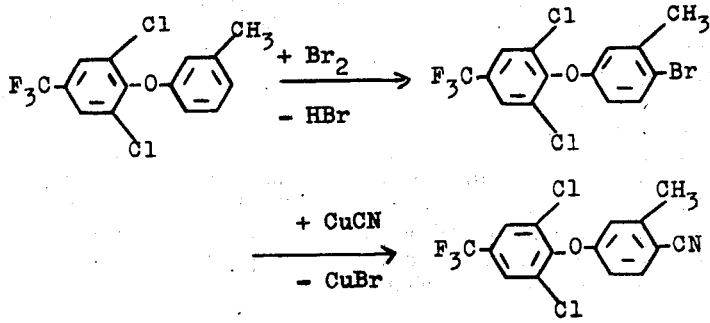

If, according to process variant (c), 2,6-dichloro-4-trifluoromethyl-3'-methoxy-4'-diazonium-diphenyl-ether cyanide and cuprous cyanide are used as starting compounds, the course of the reaction can be represented by the following formula scheme:

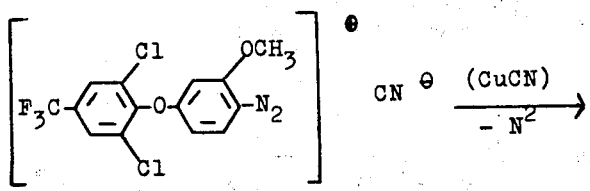

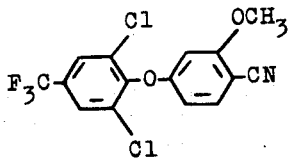

Many of the starting compounds of the formulae (II) to (VI) are known. Any which are not yet known can be prepared according to known methods (some of which are illustrated in the Examples).

Formula (II) provides a definition of the 4-halobenzotrifluorides which are used as starting compounds for variant (a). In this formula Hal preferably represents chlorine or bromine.

Formula (III) provides a definition of the phenolates which are used as starting compounds for variant (a). M preferably represents sodium or potasssium. The sodium phenolates and potassium phenolates of the formula (III) are generally known.

All aprotic solvents can be used as diluents in carrying out process variant (a). Preferred ones include amides such as hexamethylphosphoric acid triamide, dimethylformamide or dimethylacetamide and also sulfoxides, such as dimethylsulfoxide, as well as ketones, such as methyl ethyl ketone, and nitriles, such as acetonitrile.

In process variant (a), the reaction temperatures can be varied over a wide range. In general, the reaction is carried out at 40° to 200°C, preferably at 80° to 160°C.

The starting compounds of the formulae (II) and (III) used in process variant (a) are preferably reacted in stoichiometric amounts, but amounts greater or less than this by up to 20% can be used without significant losses in yield. The reaction mixture may be worked up in the manner customary in the laboratory.

Process variants (b) and (c) belong to known types of process, their novelty lying in the particular reactants used.

The preparation of the compounds of the invention is illustrated in the following Examples.

EXAMPLE 1 - Preparation of 2,6-dichloro-4-trifluoromethyl-4'-cyanodiphenyl-ether (i) Process variant (a):

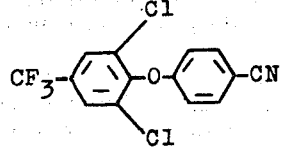

(1)

143 g (1 mol) of p-cyanophenol sodium were dissolved in 600 ml of dimethylsulfoxide. 250 g (1 mol) of 3,4,5-trichlorobenzotrifluoride were added thereto and the mixture was warmed to 140°C for six hours. After cooling, the solvent was distilled off almost completely in vacuo, and the residue was poured onto ice water. The precipitated product was extracted twice with 400 ml of methylene chloride. The organic phase was separated off, washed repeatedly with water and once with 200 ml of 20% strength sodium hydroxide solution. After drying over sodium sulfate, the solvent was removed in vacuo, and the oily residue was triturated with methanol, whereupon it crystallized and, after filtering off, was recrystallized from methanol. 166 g of 2,6-dichloro-4-trifluoromethyl-4'-cyanodiphenyl-ether of melting point 124°C were obtained representing 50% of theory.

ii. Process variant (b):

32 g (0.1 mol) of 2,6-dichloro-4'-amino-4-trifluoromethyl-diphenyl-ether were suspended in 29.5 g of 45% strength sulfuric acid. 7 g (0.1 mol) of sodium nitrite, previously dissolved in 15 ml of water, were added to the suspension cooled to 0°C. The resulting diazonium solution was poured into a solution of 45 g (0.5 mol) of cuprous cyanide and 33.1 g (0.66 mol) of sodium cyanide in 117 ml of water. The mixture was then warmed to 80°C and kept at this temperature for two hours. After cooling, the reaction mixture was extracted with toluene. The toluene phase was washed with water, and then with 10% strength sodium hydroxide solution until neutral, and was dried.

After customary working up and purification, 11.2 g of 2,6-dichloro-4'-cyano-4-trifluoromethyl-diphenyl-ether of melting point 124°C were obtained, representing 34% of theory.

2,6-Dichloro-4'-amino-4-trifluoroemethyl-diphenyl-ether (melting point from ethanol/water, 128°–130°C), used as the starting material, was obtained according to process variant (a) from sodium 4-amino-phenolate and 3,4,5-trichloro-benzotrifluoride. The reaction was carried out in dimethylsulfoxide as the diluent, at 120°–140°C.

3,4,5-Trichlorobenzotrifluoride, used as the starting material in the last paragraph, was obtained in a manner which is in principle known (see J. Am. Chem. Soc. 57, 2066–2069 (1935) and U.S. Pat. No. 2,654,789) by reaction of 4-chloro-benzotrifluoride with chlorine in the presence of 10 mol % of ferric (iron III) chloride; for this purpose, chlorine was passed into the reaction mixture, at a temperature of 60°–160°C, while stirring and using reflux cooling, until the refractive index of the reaction mixture had risen to $n_D^{20} = 1.5025$. The mixture was worked up as follows: the catalyst was filtered off and the reaction mixture distilled through a bridge. The distillate was rectified using a 1 m long silver-jacketed column. In addition to 3,4-dichlorobenzotrifluoride of refractive index $n_D^{20} = 1.4758$ and boiling point 172°–175°C, a 3,4,5- and 2,4,5-trichlorobenzotrifluoride isomer mixture of refractive index $n_D^{20} = 1.5015$ was obtained. This mixture was separated by a further vacuum distillation through a silver mirror-coated packed column (1.25 m height, with Wilson glass spiral packings of 3 mm diameter), a magnetic varpor distributor with a time interval switch serving as the column head. A vacuum of 50 mm Hg was applied at the column head; the bath temperature was 142°–150°C and the reflux ratio was 60:1. 3,4,5-Trichlorobenzotrifluoride was then collected at a temperature of 113°C. It was characterized by the NMR spectrum; the compound has a singlet at 7.65 ppm (at 6 MHz, measured in carbon tetrachloride as the solvent).

EXAMPLE 2 - Preparation of 2,6-dichloro-4'-bromo-4-trifluoromehtyl-3'-methyl-diphenyl-ether

Process variant (b):

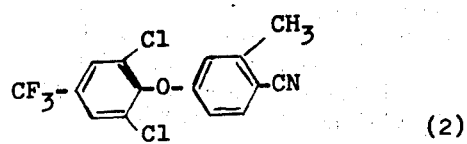

(2)

First step: 54 g (0.165 mol) of 2,6-dichloro-4-trifluoromethyl-3'-methyl-diphenyl-ether were dissolved in 200 ml of glacial acetic acid. 26.4 g (0.33 gA) of bromine were added dropwise thereto over the course of one hour. After stirring for a further three hours at 25°–30°C, the reaction mixture was poured into water. The oil which precipitated was taken up in 300 ml of methylene chloride and the solution was twice washed with 500 ml of water and dried over sodium sulfate. The solvent was stripped off in vacuo. The residue distilled.

40 g (60% of theory) of 2,6-dichloro-4'-bromo-4-trifluoromethyl-3'-methyl-diphenyl-ether were obtained.

2,6-Dichloro-4-trifluoromethyl-3'-methyl-diphenyl-ether, required as the starting material (boiling point, 3 mm : 140°C, $N_D^{22}$: 1.5380) was obtained according to process variant (a) from sodium 3-methyl-phenolate and 3,4,5-trichlorobenzotrifluoride. The reaction was carried out in dimethylsulfoxide as the diluent, at 120°C.

Second step: 30 g (0.075 mol) of 2,6-dichloro-4'-bromo-4-trifluoromethyl-3'-methyl-diphenyl-ether were dissolved in 30 ml of dimethylformamide, 7.7 g of cuprous cyanide were added and the mixture was heated to 155°C for six hours. After cooling, a solution of 36 g of ferric chloride hexahydrate, 7.3 ml of concentrated hydrochloric acid and 45 ml of water was added, and the mixture was warmed to 60°–70°C for twenty minutes. It was extracted with 300 ml of toluene and the organic phase was washed with water. After drying over sodium sulfate, the solvent was concentrated in vacuo and the residue was distilled.

5 g (18% of theory) of 2,6-dichloro-4-trifluoromethyl-4'-cyano-3'-methyl-diphenyl-ether of boiling point (3 mm Hg) 166°C were obtained; when recrystallized from methanol, this compound was obtained as a white crystalline product of melting point 104°C.

EXAMPLE 3 - Preparation of 2,6-dichloro-4-trifluoromethyl-3'-methoxy-4'-cyano-diphenyl-ether

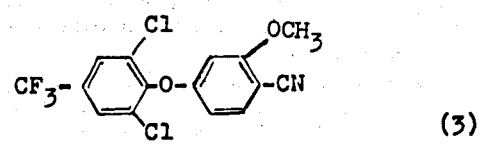

(3)

2,6-Dichloro-4-trifluoromethyl-3'-methoxy-4'-cyano-diphenyl-ether was prepared analogously to Example 2; it boiled at a boiling point (3 mm Hg) of 174°C and melted at 140°C after recrystallization from methanol.

2,6-Dichloro-4'-bromo-4-trifluoromethyl-3'-methoxy-diphenyl-ether (boiling point, 3 : 166°C, $n_D^{23}$: 1.5678) required as the starting material, was obtained according to process variant (b) by bromination of 2,6-dichloro-4-trifluoromethyl-3'-methoxy-diphenyl-ether.

2,6-Dichloro-4-trifluoromethyl-3'-methoxy-diphenyl-ether was obtained according to process variant (a) from sodium 3-methoxyphenolate and 3,4,5-trichlorobenzotrifluoride in dimethylsulfoxide at 120°C (boiling point, 3: 150°C; $n_D^{23}$ : 1.5438).

The active compounds according to the invention have excellent herbicidal properties and can therefore be used for combating weeds.

Weeds in the broadest sense are plants which grow in locations where they are not desired. As weeds there may be mentioned: dicotyledons, such as mustard (Sinapis), cress (Lepidum), cleavers (Galium), chickweed (Stellaria), camomile (Matricaria), gallant Soldier (Galinsoga), goosefoot (Chenopodium), annual nettle (Urtrica) and groundsel (Senecio), and monocotyledons, such as timothy (Phleum), bluegrass (Poa), fescue (Festuca), goosegrass (Eleusine), foxtail (Setaria), ryegrass (Lolium) and barnyard grass (Echinochloa).

The active compounds according to the invention have a very strong influence on plant growth, but in different ways, so that they can be used as selective herbicides. They display particular advantages as selective herbicides in the cultivation of cotton, rice, carrots and cereals (including maize). In higher concentrations (approximately 10 to 20 kg/ha), they can be employed as total weedkillers.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The active compounds according to the invention can be used as a mixture with other active compounds.

The formulations in general contain from 0.1 to 95 per cent by weight of active compound, preferably 0.5 to 90 per cent by weight.

The active compounds can be used as such or in the form of their formulations or the application forms prepared therefrom, such as ready-to-use solutions, emulsions, suspensions, powders, pastes and granules. They may be applied in the customary manner, for example by watering, spraying, atomizing, sprinkling and dusting.

They can be applied both post-emergence and pre-emergence; they are preferably applied after emergence of the plants.

The amount of active compound employed can vary within wide ranges. It depends essentially on the nature of the desired effect. In general, the amounts used are 0.1 to 25 kg/ha, preferably 0.5 to 10 kg/ha.

The compounds according to the invention also have an insecticidal, acaricidal and fungicidal action which deserves mention.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or their habitat a compound according to the invention alone or in the form of a composition containing as active ingredient a compound according to the invention in admixture with a diluent or carrier.

The invention also provides means of providing crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples.

Example A

Pre-emergence test

Solvent: 5 parts by weight of acetone

Emulsifier: 1 part by weight of alkylaryl polyglycol ether

To produce a suitable preparation of active compound, one part by weight of active compound was mixed with the stated amount of solvent, the stated amount of emulsifier was added and the concentrate was then diluted with water to the desired concentration.

Seeds of the test plants were sown in normal soil and, after twenty-four hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined in % damage in comparison to the development of the untreated control.

0% denotes untreated control

100% denotes total destruction

The active compounds, the amounts used and the results can be seen from Table A.

Table A

| Active compound | Amount of active compound used, kg/ha | Pre-emergence Test |||||||||
|---|---|---|---|---|---|---|---|---|---|---|
| | | Echinochloa | Chenopodium | Lolium | Stellaria | Galinsoga | Matricaria | Polygonum | Cotton | Wheat | Maize |
| 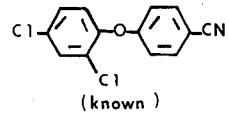 (known) | 5<br>2.5 | 60<br>60 | 20<br>0 | 20<br>0 | 20<br>20 | 40<br>20 | 40<br>0 | 20<br>0 | 20<br>0 | 0<br>0 | 20<br>0 |
| 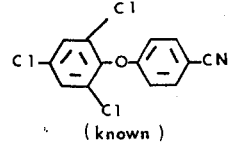 (known) | 5<br>2.5 | 40<br>20 | 20<br>20 | 20<br>20 | 60<br>40 | 40<br>40 | 40<br>20 | 0<br>0 | 0<br>0 | 20<br>0 | 0<br>0 |
| 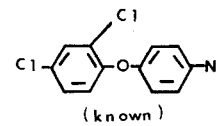 (known) | 5<br>2.5<br>1.25 | 100<br>100<br>100 | 60<br>40<br>20 | 100<br>90<br>80 | 20<br>0<br>0 | 90<br>80<br>60 | 80<br>80<br>60 | 90<br>60<br>40 | 40<br>20<br>0 | 60<br>40<br>20 | 60<br>40<br>40 |
| 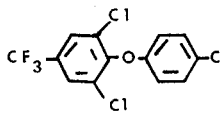 (1) | 5<br>2.5<br>1.25 | 100<br>100<br>100 | 100<br>100<br>100 | 100<br>100<br>100 | 100<br>100<br>100 | 100<br>100<br>100 | 100<br>100<br>100 | 100<br>100<br>100 | 40<br>0<br>0 | 80<br>80<br>80 | 60<br>60<br>10 |
| 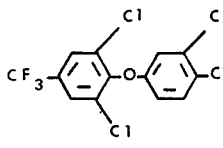 (2) | 5<br>2.5<br>1.25 | 100<br>100<br>100 | 100<br>100<br>80 | 100<br>100<br>100 | 100<br>100<br>100 | 100<br>100<br>100 | 100<br>100<br>100 | 100<br>100<br>80 | 0<br>0<br>0 | 80<br>60<br>40 | 20<br>0<br>0 |
| 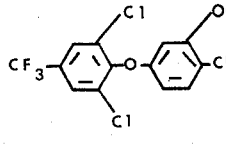 (3) | 5<br>2.5<br>1.25 | 100<br>100<br>100 | 100<br>80<br>80 | 100<br>100<br>100 | 100<br>100<br>100 | 100<br>100<br>100 | 100<br>100<br>100 | 100<br>90<br>80 | 40<br>60<br>0 | 80<br>20<br>40 | 40<br>20<br>20 |

Example B

Post-emergence test
Solvent: 5 parts by weight of acetone
Emulsifier: 1 part by weight of alkylaryl polyglycol ether To produce a suitable preparation of active compound, one part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table.

Depending on the concentration of the spray liquor, the amount of water used was between 1,000 and 2,000 liters/ha. After three weeks, the degree of damage to the plants was determined in % damage in comparison to the development of the untreated control.

0% denotes untreated control
100% denotes total destruction

The active compounds, the amounts used and the results can be seen from Table B.

Table B

| Active Compound | Amount of active compound used, kg/ha | Post-emergence Test | | | | | | | |
|---|---|---|---|---|---|---|---|---|---|
| | | Echinochloa | Chenopodium | Sinapis | Stellaria | Urtica | Cotton | Wheat | Carrots |
| Cl—⟨⟩—O—⟨⟩—CN (with Cl); (known) | 1 | 20 | 20 | 40 | 0 | 80 | 40 | 20 | 0 |
| | 0.5 | 20 | 0 | 20 | 0 | 80 | 20 | 0 | 0 |
| Cl, Cl—⟨⟩—O—⟨⟩—CN (with Cl); (known) | 1 | 0 | 20 | 20 | 0 | 40 | 20 | 40 | 0 |
| | 0.5 | 0 | 0 | 0 | 0 | 20 | 0 | 20 | 0 |
| Cl—⟨⟩—O—⟨⟩—NO₂ (with Cl); (known) | 1 | 80 | 60 | 20 | 0 | 100 | 100 | 20 | 0 |
| | 0.5 | 60 | 60 | 0 | 0 | 100 | 80 | 20 | 0 |
| CF₃—⟨Cl,Cl⟩—O—⟨⟩—CN (1) | 1 | 100 | 100 | 100 | 100 | 100 | 100 | 80 | 20 |
| | 0.5 | 100 | 100 | 100 | 100 | 100 | 100 | 80 | 0 |
| CF₃—⟨Cl,Cl⟩—O—⟨CH₃⟩—CN (2) | 1 | 80 | 100 | 90 | 100 | 100 | 0 | 40 | 0 |
| | 0.5 | 80 | 80 | 80 | 100 | 100 | 0 | 20 | 0 |
| CF₃—⟨Cl,Cl⟩—O—⟨OCH₃⟩—CN (3) | 1 | 100 | 100 | 100 | 100 | 100 | 60 | 40 | 0 |
| | 0.5 | 80 | 100 | 80 | 100 | 100 | 40 | 20 | 0 |

It will be understood that the specification and examples are illustrative but not limitative of the present invention and that other embodiments within the spirit and scope of the invention will suggest themselves to those skilled in the art.

What is claimed is:

1. Halogenated 4-trifluoromethyl-4'-cyano-diphenyl-ether compound of the formula

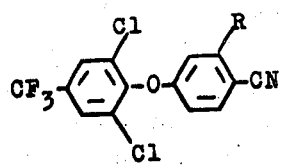

(I)

in which
R is hydrogen, halogen, alkyl of from 1 to 4 carbon atoms or alkoxy of from 1 to 4 carbon atoms.

2. Halogenated 4-trifluoromethyl-4'-cyano-diphenyl-ether compound as claimed in claim 1, wherein R is halogen.

3. Halogenated 4-trifluoromethyl-4'-cyano-diphenyl-ether compound as claimed in claim 1, wherein R is alkyl of up to 3 carbon atoms.

4. Halogenated 4-trifluoromethyl-4'-cyano-diphenyl-ether compound as claimed in claim 1, wherein R is alkoxy of up to 3 carbon atoms.

5. Halogenated 4-trifluoromethyl-4'-cyano-diphenyl-ether compound as claimed in claim 1, designated 2,6- dichloro-4-trifluoromethyl-4'-cyanodiphenyl-ether.

6. Halogenated 4-trifluoromethyl-4'-cyano-diphenyl-ether compound as claimed in claim 1, designated 2,6-dichloro-4'-cyano-4-trifluoromethyl-3'-methyl-diphenyl-ether.

7. Halogenated 4-trifluoromethyl-4'-cyano-diphenyl-ether compound as claimed in claim 1, designated 2,6-dichloro-4-trifluoromethyl-3'-methoxy-4'-cyano-diphenyl-ether.

* * * * *